United States Patent
Ren et al.

(10) Patent No.: US 8,435,771 B2
(45) Date of Patent: May 7, 2013

(54) FERMENTATION OF A LIGNOCELLULOSE-CONTAINING MATERIAL

(75) Inventors: Haiyu Ren, Beijing (CN); Hong Zhi Huang, Beijing (CN)

(73) Assignees: Novozymes A/S, Bagsvaerd (DK); CofCo Ltd., Beijing (CN)

( * ) Notice: Subject to any disclaimer, the term of this patent is extended or adjusted under 35 U.S.C. 154(b) by 277 days.

(21) Appl. No.: 12/990,526

(22) PCT Filed: May 7, 2009

(86) PCT No.: PCT/EP2009/055529
§ 371 (c)(1),
(2), (4) Date: Nov. 1, 2010

(87) PCT Pub. No.: WO2009/135898
PCT Pub. Date: Nov. 12, 2009

(65) Prior Publication Data
US 2011/0070619 A1    Mar. 24, 2011

Related U.S. Application Data

(60) Provisional application No. 61/052,775, filed on May 13, 2008, provisional application No. 61/092,829, filed on Aug. 29, 2008.

(30) Foreign Application Priority Data

May 7, 2008  (EP) ..................................... 08155828
Aug. 26, 2008  (EP) ..................................... 08162966

(51) Int. Cl.
*C12P 1/00*  (2006.01)
*C12P 7/02*  (2006.01)
*C12P 7/10*  (2006.01)
*C12N 9/00*  (2006.01)
*C12N 1/20*  (2006.01)
*C12N 15/00*  (2006.01)
*C07H 21/04*  (2006.01)

(52) U.S. Cl.
USPC ............. 435/165; 435/41; 435/155; 435/183; 435/252.3; 435/320.1; 536/23.2

(58) Field of Classification Search ........................ None
See application file for complete search history.

(56) References Cited

FOREIGN PATENT DOCUMENTS

| CN | 101289678 | 10/2008 |
|---|---|---|
| WO | WO 2005/118828 A1 | 12/2005 |
| WO | WO 2006/056838 A1 | 6/2006 |
| WO | WO2006056838 * | 6/2006 |
| WO | WO 2007/134607 A1 | 11/2007 |
| WO | WO2007134607 * | 11/2007 |
| WO | WO 2008/095098 A2 | 8/2008 |

OTHER PUBLICATIONS

Lau et al. Biotechnol Bioeng. Feb. 15, 2008;99(3):529-39.*
Georgieva et al., "Enzymatic Hydrolysis and Ethanol Fermentation of High Dry Matter Wet-Exploded Wheat Straw at Low Enzyme Loading", Applied Biochem Biotechnol, vol. 148, pp. 35-44 (2008).
Lau et al., "Ethanolic Fermentation of Hydrolysates From Ammonia Fiber Expansion (AFEX) Treated Corn Stover and Distillers Grain Without Detoxification and External Nutrient Supplementation", Biotechnology and Bioengineering, vol. 99, No. 3, pp. 529-539 (2008).
Ohgren et al., "Fuel Ethanol Production From Steam-Pretreated Corn Stover Using SSF At Higher Dry Matter Content", Biomass and Bioenergy, vol. 30, pp. 863-569 (2006).
Olofsson et al., "A short review on SSF—an interesting process option for ethanol production from lignocellulosic feedstocks", Biotechnology for Biofuels, vol. 1, No. 7, pp. 1-14 (2008).
Panagiotou et al., "Effect of Compounds Released During Pretreatment of Wheat Straw on Microbial Growth and Enzymatic Hydrolysis Rates", Biotechnology and Bioengineering, vol. 96, No. 2, pp. 250-258 (2007).
Sassner et al., "Bioethanol Production Based on Simultaneous Saccharification and Fermentation of Steam-Pretreated Salix at High Dry-Matter Content", Enzyme and Microbial Technology, vol. 39, pp. 756-762 (2006).

* cited by examiner

*Primary Examiner* — Christian Fronda
(74) *Attorney, Agent, or Firm* — Elias Lambiris

(57) ABSTRACT

The invention relates to a process of fermenting a hydrolysed pre-treated lignocellulose-containing material to produce a fermentation product.

17 Claims, No Drawings

FERMENTATION OF A LIGNOCELLULOSE-CONTAINING MATERIAL

CROSS-REFERENCE TO RELATED APPLICATIONS

This application is a 35 U.S.C. 371 national application of PCT/EP2009/055529 filed May 7, 2009 which claims priority or the benefit under 35 U.S.C. 119 of European application nos. 08155828.0 and 08162966.9 filed May 7, 2008 and Aug. 26, 2008, respectively, and U.S. provisional application Nos. 61/052,775 and 61/092,829 filed May 13, 2008 and Aug. 29, 2008, respectively, the contents of which are fully incorporated herein by reference.

TECHNICAL FIELD

The present invention relates to fermentation processes based on lignocellulose-containing material.

BACKGROUND OF THE INVENTION

Due to the limited reserves of fossil fuels and worries about emission of greenhouse gases there is an increasing focus on using renewable energy sources.

Plant material comprising lignocellulose-containing material can be converted into fermentable sugars and used as an energy source by fermenting organisms including bacteria, yeast and fungi for industrial purposes. For example, Lignocellulose-containing material can be converted into sugars by enzymes, and the resulting sugars can be used as a feedstock for industrial microorganisms to produce products such as plastics and ethanol.

Production of fermentation products, such as ethanol, from fermentation of lignocellulose-containing material is known in the art and conventionally includes pretreatment, hydrolysis, and fermentation of the lignocellulose-containing material.

Pre-treatment lignocellulose-containing material results in the release of, e.g., acetic acid, phenolics and furans, from the lignocellulose-containing material that may irreversibly bind enzymes added during hydrolysis and fermentation. These compounds may also be toxic to the fermenting organism's metabolism and inhibit the performance of the fermenting organism. To overcome this inhibition of yeast it has been practised to dilute the hydrolyzate and ferment at a low dry solids concentration thereby achieving a corresponding dilution of the concentration of the inhibitory compounds.

It is also well known that by increasing the pH the toxicity of especially the acetic acid and other weak acids to the yeast can be reduced. However, in order to control contamination by spoilage bacteria the fermentation of hydrolysed lignocellulose-containing material is generally performed at acid pH (below 5.5). Thus, fermentation of hydrolysed lignocellulose-containing material is usually performed at a low pH and in low dry solids concentrations.

There is a need for improved processes for production of fermentation products from lignocellulose-containing material.

SUMMARY OF THE INVENTION

The present inventors have now discovered that it is possible to ferment a mash of hydrolysed lignocellulose-containing material at a higher pH and to control contamination by spoilage bacteria at the same time. This is achieved by using a very high dry solids concentration during fermentation. Without being bound by theory it is believed that while the toxicity to the fermenting organism of the weak acids, such as acetic acid, is reduced at the high pH thereby allowing proliferation of the fermenting organism the growth of spoilage bacteria is controlled by a high concentration of other inhibitory compounds.

Accordingly, the invention relates in a first aspect to processes for producing a fermentation product from lignocellulose-containing material, comprising the steps of, (a)(i) pre-treating a lignocellulose-containing material, (a)(ii) hydrolyzing the pre-treated lignocellulose-containing material, (b) fermenting the hydrolyzate obtained in step (a) using a fermenting organism, and (c) optionally recovering the fermentation product, wherein during the fermentation in step (b) the pH is from 5.5 to 9.0 and the high dry solids concentration is at least 20%.

In a second aspect the invention relates to processes for producing a fermentation product said process comprising, (a) providing a hydrolyzate of a pre-treated lignocellulose-containing material, (b) contacting the hydrolyzate with a fermenting organism to produce a fermentation product, and (c) optionally recovering the fermentation product, wherein during the fermentation in step (b) the pH is from 5.5 to 9.0 and the high dry solids concentration is at least 20%.

In the above aspects the fermenting organism is preferably a yeast and the fermentation product is preferably ethanol.

More details on the steps for the above aspects are described below, e.g., in the sections "Pre-treatment", "Hydrolysis" and "Fermentation".

DETAILED DESCRIPTION OF THE INVENTION

Lignocellulose-Containing Material

The term "lignocellulose-containing material" used herein refers to material that primarily consists of cellulose, hemicellulose, and lignin. The term is synonymous with "lignocellulosic material". Such material is often referred to as "biomass".

Any lignocellulose-containing material is contemplated according to the present invention. The lignocellulose-containing material may be any material containing lignocellulose. In a preferred embodiment the lignocellulose-containing material contains at least 30 wt. %, preferably at least 50 wt. %, more preferably at least 70 wt. %, even more preferably at least 90 wt. % lignocellulose. It is to be understood that the lignocellulose-containing material may also comprise other constituents such as proteinaceous material, starch, sugars, such as fermentable sugars and/or un-fermentable sugars.

Lignocellulose-containing material is generally found, for example, in the stems, leaves, hulls, husks, and cobs of plants or leaves, branches, and wood of trees. Lignocellulose-containing material can also be, but is not limited to, herbaceous material, agricultural residues, forestry residues, municipal solid wastes, waste paper, and pulp and paper mill residues. It is understood herein that lignocellulose-containing material may be in the form of plant cell wall material containing lignin, cellulose, and hemi-cellulose in a mixed matrix.

In a preferred embodiment the lignocellulose-containing material comprises one or more of corn stover, corn fiber, rice straw, pine wood, wood chips, poplar, bagasse, paper and pulp processing waste.

Other examples of lignocellulose-containing material include hardwood, such as poplar and birch, softwood, cereal straw, such as wheat straw, switchgrass, municipal solid waste, industrial organic waste, office paper, or mixtures thereof.

In a preferred embodiment the lignocellulosic material is corn stover or corn fiber, preferably pretreated by steam explosion, preferably enzymatically hydrolysed, and fermented at pH around 6 at a dry solids concentration of around 30% with a yeast to produce ethanol. The ethanol is preferably recovered for use as fuel ethanol.

Pre-Treatment

The structure of lignocellulose is not directly accessible to enzymatic hydrolysis. Therefore, the lignocellulose-containing material has to be pre-treated, e.g., by acid hydrolysis under adequate conditions of pressure and temperature, in order to break the lignin seal and disrupt the crystalline structure of cellulose. This causes solubilization of the hemicellulose and cellulose fractions. The cellulose and hemicellulose can then be hydrolyzed enzymatically, e.g., by cellulase enzymes (cellulolytic enzymes), to convert the carbohydrate polymers into fermentable sugars which, using a fermenting organism, e.g. a yeast, may be fermented into a desired fermentation product, such as ethanol. Optionally the fermentation product may be recovered, e.g., by distillation.

When lignocellulose-containing material is pre-treated, degradation products that may inhibit enzymes and/or may be toxic to fermenting organisms are produced. These degradation products severely decrease both the hydrolysis and fermentation rate.

Methods for pre-treating lignocellulose-containing material are well known in the art. Examples of contemplated methods are described below in the section "Pre-treatment".

The pre-treated lignocellulose degradation products include lignin degradation products, cellulose degradation products and hemicellulose degradation products. The pre-treated lignin degradation products may be phenolics in nature.

The hemicellulose degradation products include furans from sugars (such as hexoses and/or pentoses), including xylose, mannose, galactose, rhamanose, and arabinose. Examples of hemicelluloses include xylan, galactoglucomannan, arabinogalactan, arabinoglucuronoxylan, glucuronoxylan, and derivatives and combinations thereof.

Examples of inhibitory compounds, i.e., pre-treated lignocellulose degradation products, include 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallollol, pyrogallol mono methyl ether, vanillyl alcohol, vanillin, isovanillin, vanillic acid, isovanillic acid, homovanillic acid, veratryl alcohol, veratraldehyde, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxy methylfurfural, 5-hydroxy methylfurfural, formic acid, acetic acid, levulinic acid, cinnamic acid, coniferyl aldehyde, isoeugenol, hydroquinone, eugenol or combinations thereof. Other inhibitory compounds can be found in, e.g., Luo et al., 2002, Biomass and Bioenergy 22: 125-138.

The lignocellulose-containing material may be pre-treated in any suitable way. Pre-treatment may be carried out before and/or during hydrolysis and/or fermentation. In a preferred embodiment the pre-treated material is hydrolyzed, preferably enzymatically, before and/or during fermentation. The goal of pre-treatment is to separate and/or release cellulose; hemicellulose and/or lignin and this way improve the rate of hydrolysis. Pre-treatment methods such as wet-oxidation and alkaline pre-treatment targets lignin, while dilute acid and auto-hydrolysis targets hemicellulose. Steam explosion is an example of a pre-treatment that targets cellulose.

According to the invention the pre-treatment applied in step (a) may be a conventional pre-treatment step using techniques well known in the art. Examples of suitable pre-treatments are disclosed below. In a preferred embodiment pre-treatment takes place in aqueous slurry.

The lignocellulose-containing material may during pre-treatment be present in a dry solids concentration of between 10-80 wt. %, preferably between 20-70 wt. %, especially between 30-60 wt. %, such as around 50 wt. %.

Chemical, Mechanical and/or Biological Pre-Treatment

The lignocellulose-containing material may according to the invention be chemically, mechanically and/or biologically pre-treated before hydrolysis and/or fermentation. Mechanical treatment (often referred to as physical treatment) may be used alone or in combination with subsequent or simultaneous hydrolysis, especially enzymatic hydrolysis.

Preferably, chemical, mechanical and/or biological pre-treatment is carried out prior to the hydrolysis and/or fermentation. Alternatively, the chemical, mechanical and/or biological pre-treatment may be carried out simultaneously with hydrolysis, such as simultaneously with addition of one or more cellulase enzymes (cellulolytic enzymes), or other enzyme activities mentioned below, to release, e.g., fermentable sugars, such as glucose and/or maltose.

In an embodiment of the invention the pre-treated lignocellulose-containing material may be washed. However, washing is not mandatory and is in a preferred embodiment eliminated.

Chemical Pre-Treatment

The term "chemical treatment" refers to any chemical pre-treatment which promotes the separation and/or release of cellulose, hemicellulose and/or lignin. Examples of suitable chemical pre-treatments include treatment with; for example, dilute acid, lime, alkaline, organic solvent, ammonia, sulfur dioxide, carbon dioxide. Further, wet oxidation and pH-controlled hydrothermolysis are also considered chemical pre-treatment.

In a preferred embodiment the chemical pre-treatment is acid treatment, more preferably, a continuous dilute and/or mild acid treatment, such as, treatment with sulfuric acid, or another organic acid, such as acetic acid, citric acid, tartaric acid, succinic acid, hydrogen chloride or mixtures thereof. Other acids may also be used. Mild acid treatment means that the treatment pH lies in the range from 1-5, preferably 1-3. In a specific embodiment the acid concentration is in the range from 0.1 to 2.0 wt. % acid, preferably sulphuric acid. The acid may be contacted with the lignocellulose-containing material and the mixture may be held at a temperature in the range of 160-220° C., such as 165-195° C., for periods ranging from minutes to seconds, e.g., 1-60 minutes, such as 2-30 minutes or 3-12 minutes. Addition of strong acids, such as sulphuric acid, may be applied to remove hemicellulose. This enhances the digestibility of cellulose.

Other techniques are also contemplated. Cellulose solvent treatment has been shown to convert about 90% of cellulose to glucose. It has also been shown that enzymatic hydrolysis could be greatly enhanced when the lignocellulose structure is disrupted. Alkaline $H_2O_2$, ozone, organosolv (uses Lewis acids, $FeCl_3$, $(Al)_2SO_4$ in aqueous alcohols), glycerol, dioxane, phenol, or ethylene glycol are among solvents known to disrupt cellulose structure and promote hydrolysis (Mosier et al., 2005, Bioresource Technology 96: 673-686).

Alkaline chemical pre-treatment with base, e.g., NaOH, $Na_2CO_3$ and/or ammonia or the like, is also contemplated according to the invention. Pre-treatment methods using ammonia are described in, e.g., WO 2006/110891, WO 2006/

110899, WO 2006/110900, and WO 2006/110901 (which are hereby incorporated by reference).

Wet oxidation techniques involve use of oxidizing agents, such as: sulphite based oxidizing agents or the like. Examples of solvent pre-treatments include treatment with DMSO (Dimethyl Sulfoxide) or the like. Chemical pre-treatment is generally carried out for 1 to 60 minutes, such as from 5 to 30 minutes, but may be carried out for shorter or longer periods of time dependent on the material to be pre-treated.

Other examples of suitable pre-treatment methods are described by Schell et al., 2003, *Appl. Biochem and Biotechn. Vol.* 105-108: 69-85, and Mosier et al., 2005, *Bioresource Technology* 96: 673-686, and U.S. Publication No. 2002/0164730, which references are hereby all incorporated by reference.

Mechanical Pre-Treatment

The term "mechanical pre-treatment" refers to any mechanical (or physical) treatment which promotes the separation and/or release of cellulose, hemicellulose and/or lignin from lignocellulose-containing material. For example, mechanical pre-treatment includes various types of milling, irradiation, steaming/steam explosion, and hydrothermolysis.

Mechanical pre-treatment includes comminution (mechanical reduction of the size). Comminution includes dry milling, wet milling and vibratory ball milling. Mechanical pre-treatment may involve high pressure and/or high temperature (steam explosion). In an embodiment of the invention high pressure means pressure in the range from 300 to 600 psi, preferably 400 to 500 psi, such as around 450 psi. In an embodiment of the invention high temperature means temperatures in the range from about 100 to 300° C., preferably from about 140 to 235° C. In a preferred embodiment mechanical pre-treatment is a batch-process, steam gun hydrolyzer system which uses high pressure and high temperature as defined above. A Sunds Hydrolyzer (available from Sunds Defibrator AB (Sweden) may be used for this.

Combined Chemical and Mechanical Pre-Treatment

In a preferred embodiment both chemical and mechanical pre-treatments are carried out. For instance, the pre-treatment step may involve dilute or mild acid treatment and high temperature and/or pressure treatment. The chemical and mechanical pre-treatment may be carried out sequentially or simultaneously, as desired.

Accordingly in a preferred embodiment, the lignocellulose-containing material is subjected to both chemical and mechanical pre-treatment to promote the separation and/or release of cellulose, hemicellulose and/or lignin.

In a preferred embodiment the pre-treatment is carried out as a dilute and/or mild acid steam explosion step. In another preferred embodiment pre-treatment is carried out as an ammonia fiber explosion step (or AFEX pre-treatment step).

Biological Pre-Treatment

As used in the present invention the term "biological pre-treatment" refers to any biological pre-treatment which promotes the separation and/or release of cellulose, hemicellulose, and/or lignin from the lignocellulose-containing material. Biological pre-treatment techniques can involve applying lignin-solubilizing microorganisms (see, for example, Hsu, 1996, Pretreatment of biomass, in *Handbook on Bioethanol: Production and Utilization*, Wyman, ed., Taylor & Francis, Washington, D.C., 179-212; Ghosh and Singh, 1993, Physicochemical and biological treatments for enzymatic/microbial conversion of lignocellulosic biomass, *Adv. Appl. Microbiol.* 39: 295-333; McMillan, 1994, Pretreating lignocellulosic biomass: a review, in *Enzymatic Conversion of Biomass for Fuels Production*, Himmel, Baker, and Overend, eds., ACS Symposium Series 566, American Chemical Society, Washington, D.C., chapter 15; Gong, Cao, Du, and Tsao, 1999, Ethanol production from renewable resources, in *Advances in Biochemical Engineering/Biotechnology*, Scheper, ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Hydrolysis

Before and/or simultaneously with fermentation the pre-treated lignocellulose-containing material may be hydrolyzed to break down cellulose and hemicellulose.

The dry solids content during hydrolysis may be in the range from 5-50 wt. %, preferably 10-40 wt. %, preferably 20-30 wt. %. Hydrolysis may in a preferred embodiment be carried out as a fed batch process where the pre-treated lignocellulose-containing material (substrate) is fed gradually to an, e.g., enzyme containing hydrolysis solution.

In a preferred embodiment hydrolysis is carried out enzymatically. According to the invention the pre-treated lignocellulose-containing material may be hydrolyzed by one or more hydrolases (class EC 3 according to Enzyme Nomenclature), preferably one or more carbohydrases selected from the group consisting of cellulase, hemicellulase, amylase, such as alpha-amylase, protease, carbohydrate-generating enzyme, such as glucoamylase, esterase, such as lipase. Alpha-amylase, glucoamylase and/or the like may be present during hydrolysis and/or fermentation as the lignocellulose-containing material may include some starch.

The enzyme(s) used for hydrolysis is (are) capable of directly or indirectly converting carbohydrate polymers into fermentable sugars which can be fermented into a desired fermentation product, such as ethanol.

In a preferred embodiment the carbohydrase has cellulase enzyme activity. Suitable carbohydrases are described in the "Enzymes"-section below.

Hemicellulose polymers can be broken down by hemicellulases and/or acid hydrolysis to release its five and six carbon sugar components. The six carbon sugars (hexoses), such as glucose, galactose, arabinose, and mannose, can readily be fermented to, e.g., ethanol, acetone, butanol, glycerol, citric acid, fumaric acid, etc. by suitable fermenting organisms including yeast. Preferred for ethanol fermentation is yeast of the species *Saccharomyces cerevisiae*, preferably strains which are resistant towards high levels of ethanol, i.e., up to, e.g., about 10, 12 or 15 vol. % ethanol or more, such as 20 vol. % ethanol.

In a preferred embodiment the pre-treated lignocellulose-containing material is hydrolyzed using a hemicellulase, preferably a xylanase, esterase, cellobiase, or combination thereof.

Hydrolysis may also be carried out in the presence of a combination of hemicellulases and/or cellulases, and optionally one or more of the other enzyme activities mentioned in the "Enzyme" section below.

Enzymatic treatments may be carried out in a suitable aqueous environment under conditions which can readily be determined by one skilled in the art.

In a preferred embodiment hydrolysis is carried out at suitable, preferably optimal conditions for the enzyme(s) in question.

Suitable process time, temperature and pH conditions can readily be determined by one skilled in the art present invention. Preferably, hydrolysis is carried out at a temperature between 25 and 70° C., preferably between 40 and 60° C., especially around 50° C. The process is preferably carried out at a pH in the range from 3-8, preferably pH 4-6, especially around pH 5.

Preferably, hydrolysis is carried out for between 12 and 96 hours, preferable 16 to 72 hours, more preferably between 24 and 48 hours.

Fermentation

According to the invention the pre-treated (and hydrolyzed) lignocellulose-containing material is fermented by at least one fermenting organism capable of fermenting fermentable sugars, such as glucose, xylose, mannose, and galactose directly or indirectly into a desired fermentation product.

The pH during the fermentation is in the range from 5.5 to 9.0, preferably at from 5.7 to 8.0, more preferably from 5.8 to 7.0, and most preferably at least pH 5.9 to 6.5, such as around pH 6. The pH may be adjusted using any suitable compound. In a preferred embodiment the pH is adjusted using NaOH.

The dry solids concentration during the fermentation is in the range of at around 20% and up to around 35%, such as at least 20%, at least 21%, at least 22%, at least 23%, at least 25%, at least 26%, at least 27%, at least 28%, at least 29%, and up to around 30%, up to 31%, up to at 32%, up to 33% or even up to 34%.

The fermentation is preferably ongoing for between 8 to 96 hours, preferably 12 to 72 hours, more preferable from 24 to 48 hours.

In an embodiment the fermentation is carried out at a temperature between 20 to 40° C., preferably 26 to 34° C., in particular around 32° C. In an embodiment the pH is from pH 5.5 to 9.0, preferably from around pH 6 to pH 6.5.

According to the invention hydrolysis in step (a) and fermentation in step (b) may be carried out simultaneously (SSF process) or sequentially (SHF process) or as a hybrid hydrolysis and fermentation (HHF).

In a preferred embodiment hydrolysis and fermentation is carried out as a simultaneous hydrolysis and fermentation step (SSF). In general this means that combined/simultaneous hydrolysis and fermentation are carried out at conditions (e.g., temperature and/or pH) suitable, preferably optimal, for the fermenting organism(s) in question.

In an embodiment there is no separate holding stage for the hydrolysis, meaning that the hydrolyzing enzyme(s) and the fermenting organism are added together. When the fermentation (e.g., ethanol fermentation using Saccharomyces yeast) is performed simultaneously with hydrolysis the temperature is preferably between 26° C. and 35° C., more preferably between 30° C. and 34° C., such as around 32° C. A temperature program comprising at least two holding stages at different temperatures may be applied according to the invention.

In another preferred embodiment hydrolysis and fermentation are carried out as hybrid hydrolysis and fermentation (HHF). HHF typically begins with a separate partial hydrolysis step and ends with a simultaneous hydrolysis and fermentation step. The separate partial hydrolysis step is an enzymatic cellulose saccharification step typically carried out at conditions (e.g., at higher temperatures) suitable, preferably optimal, for the hydrolyzing enzyme(s) in question. The subsequent simultaneous hydrolysis and fermentation step is typically carried out at conditions suitable for the fermenting organism(s) (often at lower temperatures than the separate hydrolysis step). Finally, hydrolysis and fermentation may also be carried out a separate hydrolysis and fermentation, where the hydrolysis is taken to completion before initiation of fermentation. This is often referred to as "SHF".

Recovery

Subsequent to fermentation the fermentation product may be separated from the fermentation medium/broth. The medium/broth may be distilled to extract the fermentation product or the fermentation product may be extracted from the fermentation medium/broth by micro or membrane filtration techniques. Alternatively the fermentation product may be recovered by stripping. Recovery methods are well known in the art.

Fermentation Products

Processes of the invention may be used for producing any fermentation product. Especially contemplated fermentation products include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones.

In a preferred embodiment the fermentation product is an alcohol, especially ethanol. The fermentation product, such as ethanol, obtained according to the invention, may preferably be fuel alcohol/ethanol. However, in the case of ethanol it may also be used as potable ethanol.

Fermenting Organism

The term "fermenting organism" refers to any organism, including bacterial and fungal organisms, suitable for producing a desired fermentation product. Especially suitable fermenting organisms according to the invention are able to ferment, i.e., convert, sugars, such as glucose, directly or indirectly into the desired fermentation product. Examples of fermenting organisms include fungal organisms, such as yeast. Preferred yeast includes strains of the genus *Saccharomyces*, in particular a strain of *Saccharomyces cerevisiae* or *Saccharomyces uvarum*; a strain of *Pichia*, in particular *Pichia stipitis* or *Pichia pastoris*; a strain of the genus *Candida*, in particular a strain of *Candida utilis, Candida arabinofermentans, Candida diddensii,* or *Candida boidinii*. Other contemplated yeast includes strains of *Hansenula*, in particular *Hansenula polymorpha* or *Hansenula anomala*; strains of *Kluyveromyces*, in particular *Kluyveromyces marxianus* or *Kluyveromyces fagilis*, and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter* in particular *Zymobactor palmae*, strains of *Klebsiella*, in particular *Klebsiella oxytoca*, strains of *Leuconostoc*, in particular *Leuconostoc mesenteroides*, strains of *Clostridium*, in particular *Clostridium butyricum*, strains of *Enterobacter* in particular *Enterobacter aerogenes* and strains of *Thermoanaerobacter*, in particular *Thermoanaerobacter* BG1L1 (*Appl. Micrbiol. Biotech.* 77: 61-86) and *Thermoanarobacter ethanolicus*.

Commercially available yeast includes, e.g., RED STAR™ or ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Enzymes

Even though not specifically mentioned in context of processes of the invention, it is to be understood that the enzymes (as well as other compounds) are used in an "effective amount".

Cellulolytic Enzymes

One or more cellulolytic enzymes may be present during fermentation, hydrolysis, SHF or HHF.

The terms "cellulolytic enzymes" as used herein are understood as comprising the cellobiohydrolases (EC 3.2.1.91), e.g., cellobiohydrolase I and cellobiohydrolase II, as well as the endo-glucanases (EC 3.2.1.4) and beta-glucosidases (EC 3.2.1.21). See relevant sections below with further description of such enzymes.

In order to be efficient, the digestion of cellulose may require several types of enzymes acting cooperatively. At least three categories of enzymes are often needed to convert cellulose into glucose: endoglucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases are the key enzymes for the degradation of native crystalline cellulose. The term "cellobiohydrolase I" is defined herein as a cellulose 1,4-beta-cellobiosidase (also referred to as Exo-glucanase, Exo-cellobiohydrolase or 1,4-beta-cellobiohydrolase) activity, as defined in the enzyme class EC 3.2.1.91, which catalyzes the hydrolysis of 1,4-beta-D-glucosidic linkages in cellulose and cellotetraose, by the release of cellobiose from the non-reducing ends of the chains. The definition of the term "cellobiohydrolase II activity" is identical, except that cellobiohydrolase II attacks from the reducing ends of the chains.

The cellulolytic enzyme may comprise a carbohydrate-binding module (CBM) which enhances the binding of the enzyme to a lignocellulose-containing fiber and increases the efficacy of the catalytic active part of the enzyme. A CBM is defined as contiguous amino acid sequence within a carbohydrate-active enzyme with a discreet fold having carbohydrate-binding activity. For further information of CBMs see the CAZy internet server (Supra) or Tomme et al. (1995) in Enzymatic Degradation of Insoluble Polysaccharides (Saddler and Penner, eds.), Cellulose-binding domains: classification and properties. pp. 142-163, American Chemical Society, Washington.

In a preferred embodiment the cellulolytic enzymes may be a cellulolytic preparation as defined in U.S. application No. 60/941,251, which is hereby incorporated by reference. In a preferred embodiment the cellulolytic preparation comprising a polypeptide having cellulolytic enhancing activity (GH61A), preferably the *Thermoascus aurantiacus* GH61A disclosed in WO 2005/074656 (hereby incorporated by reference). The cellulolytic preparation may further comprise a beta-glucosidase, such as a beta-glucosidase derived from a strain of the genus *Humicola, Trichoderma, Aspergillus* or *Penicillium*, including the *Humicola insolens* CEL45A endoglucanase core/*Aspergillus oryzae* beta-glucosidase fusion protein disclosed in U.S. application no. U.S. Ser. No. 11/781, 151 or PCT/US2007/074038 (Novozymes). In an embodiment the cellulolytic preparation may also comprise a CBH II, preferably *Thielavia terrestris* cellobiohydrolase II (CEL6A). In an embodiment the cellulolytic preparation also comprises a cellulase enzymes preparation, preferably the one derived from *Trichoderma reesei*.

The cellulolytic activity may, in a preferred embodiment, be derived from a fungal source, such as a strain of the genus *Trichoderma*, preferably a strain of *Trichoderma reesei*; or a strain of the genus *Humicola*, such as a strain of *Humicola insolens*; or a strain of *Chrysosporium*, preferably a strain of *Chrysosporium lucknowense*.

In an embodiment the cellulolytic enzyme preparation comprises a polypeptide having cellulolytic enhancing activity (GH61A) disclosed in WO 2005/074656; a cellobiohydrolase, such as *Thielavia terrestris* cellobiohydrolase II (CEL6A), a beta-glucosidase (e.g., the fusion protein disclosed in U.S. application No. 60/832,511) and cellulolytic enzymes, e.g., derived from *Trichoderma reesei*.

In an embodiment the cellulolytic enzyme is the commercially available product CELLUCLAST® 1.5L or CELLUZYME™ available from Novozymes A/S, Denmark or ACCELERASE™ 1000 (from Genencor Inc. USA).

A cellulolytic enzyme may be added for hydrolyzing the pre-treated lignocellulose-containing material. The cellulolytic enzyme may be dosed in the range from 0.1-100 FPU per gram dry solids, preferably 0.5-50 FPU per gram dry solids, especially 1-20 FPU per gram dry solids.

The cellulolytic enzyme may be dosed in the range from 1-1000 EGU per gram dry solids, preferably 10-500 EGU per gram dry solids, especially 50 to 200 EGU per gram dry solids.

In another embodiment at least 1 mg cellulolytic enzyme per gram dry solids (DS), preferably at least 3 mg cellulolytic enzyme per gram dry solids, such as between 5 and 10 mg cellulolytic enzyme(s) is (are) used for hydrolysis.

Endoglucanase (EG)

Endoglucanases (EC No. 3.2.1.4) catalyses endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucanohydrolase, but the abbreviated term endoglucanase is used in the present specification. Endoglucanase activity may be determined using carboxy methyl cellulose (CMC) hydrolysis according to the procedure of Ghose, 1987, *Pure and Appl. Chem.* 59: 257-268.

In a preferred embodiment endoglucanases may be derived from a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium lucknowense*.

Cellobiohydrolase (CBH)

The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain.

Examples of cellobiohydroloses are mentioned above including CBH I and CBH II from *Trichoderma reseei*; *Humicola insolens* and CBH II from *Thielavia terrestris* cellobiohydrolase (CELL6A)

Cellobiohydrolase activity may be determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. The Lever et al. method is suitable for assessing hydrolysis of cellulose in corn stover and the method of van Tilbeurgh et al. is suitable for determining the cellobiohydrolase activity on a fluorescent disaccharide derivative.

Beta-Glucosidase

One or more beta-glucosidases (sometimes referred to as "cellobiases") may be present during hydrolysis, fermentation, SHF or HHF.

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 pmole of p-nitrophenol produced per minute at 50° C., pH 5 from 4 mM p-nitrophenyl-beta-D-glucopyranoside as substrate in 100 mM sodium citrate, 0.01% TWEEN® 20.

In a preferred embodiment the beta-glucosidase is of fungal origin, such as a strain of the genus *Trichoderma*, *Aspergillus* or *Penicillium*. In a preferred embodiment the beta-glucosidase is a derived from *Trichoderma reesei*, such as the beta-glucosidase encoded by the bgl1 gene (see FIG. 1 of EP 562003). In another preferred embodiment the beta-glucosidase is derived from *Aspergillus oryzae* (recombinantly produced in *Aspergillus oryzae* according to WO 02/095014), *Aspergillus fumigatus* (recombinantly produced in *Aspergillus oryzae* according to Example 22 of WO 02/095014) or *Aspergillus niger* (1981, *J. Appl.* 3: 157-163).

Cellulolytic Enhancing Activity

The term "cellulolytic enhancing activity" is defined herein as a biological activity that enhances the hydrolysis of a lignocellulose derived material by proteins having cellulolytic activity. For purposes of the present invention, cellulolytic enhancing activity is determined by measuring the increase in reducing sugars or in the increase of the total of cellobiose and glucose from the hydrolysis of a lignocellulose derived material, e.g., pre-treated lignocellulose-containing material by cellulolytic protein under the following conditions: 1-50 mg of total protein/g of cellulose in PCS (pre-treated corn stover), wherein total protein is comprised of 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/g of cellulose in PCS).

The polypeptides having cellulolytic enhancing activity enhance the hydrolysis of a lignocellulose derived material catalyzed by proteins having cellulolytic activity by reducing the amount of cellulolytic enzyme required to reach the same degree of hydrolysis preferably at least 0.1-fold, more at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

In a preferred embodiment the hydrolysis and/or fermentation is carried out in the presence of a cellulolytic enzyme in combination with a polypeptide having enhancing activity. In a preferred embodiment the polypeptide having enhancing activity is a family GH61A polypeptide. WO 2005/074647 discloses isolated polypeptides having cellulolytic enhancing activity and polynucleotides thereof from *Thielavia terrestris*. WO 2005/074656 discloses an isolated polypeptide having cellulolytic enhancing activity and a polynucleotide thereof from *Thermoascus aurantiacus*. U.S. Application Publication No. 2007/0077630 discloses an isolated polypeptide having cellulolytic enhancing activity and a polynucleotide thereof from *Trichoderma reesei*.

Hemicellulolytic Enzymes

According to the invention the pre-treated lignocellulose-containing material may further be subjected to one or more hemicellulolytic enzymes, e.g., one or more hemicellulases.

Hemicellulose can be broken down by hemicellulases and/or acid hydrolysis to release its five and six carbon sugar components.

In an embodiment of the invention the lignocellulose derived material may be treated with one or more hemicellulases.

Any hemicellulase suitable for use in hydrolyzing hemicellulose, preferably into xylose, may be used. Preferred hemicellulases include xylanases, arabinofuranosidases, acetyl xylan esterase, feruloyl esterase, glucuronidases, endo-galactanase, mannases, endo or exo arabinases, exo-galactanses, and mixtures of two or more thereof. Preferably, the hemicellulase for use in the present invention is an exo-acting hemicellulase, and more preferably, the hemicellulase is an exo-acting hemicellulase which has the ability to hydrolyze hemicellulose under acidic conditions of below pH 7, preferably pH 3-7. An example of hemicellulase suitable for use in the present invention includes VISCOZYME™ (available from Novozymes A/S, Denmark).

In an embodiment the hemicellulase is a xylanase. In an embodiment the xylanase may preferably be of microbial origin, such as of fungal origin (e.g., *Trichoderma*, *Meripilus*, *Humicola*, *Aspergillus*, *Fusarium*) or from a bacterium (e.g., *Bacillus*). In a preferred embodiment the xylanase is derived from a filamentous fungus, preferably derived from a strain of *Aspergillus*, such as *Aspergillus aculeatus*; or a strain of *Humicola*, preferably *Humicola lanuginosa*. The xylanase may preferably be an endo-1,4-beta-xylanase, more preferably an endo-1,4-beta-xylanase of GH10 or GH11. Examples of commercial xylanases include SHEARZYME™ and BIOFEED WHEAT™ from Novozymes A/S, Denmark.

The hemicellulase may be added in an amount effective to hydrolyze hemicellulose, such as, in amounts from about 0.001 to 0.5 wt.-% of dry solids, more preferably from about 0.05 to 0.5 wt.-% of dry solids.

Xylanases may be added in amounts of 0.001-1.0 g/kg dry solids, preferably in the amounts of 0.005-0.5 g/kg dry solids, and most preferably from 0.05-0.10 g/kg dry solids.

Other Enzymes

Other hydrolytic enzymes may also be present during hydrolysis, fermentation, SHF or HHF. Contemplated enzymes include alpha-amylases; glucoamylases or another carbohydrate-source generating enzymes, such as beta-amylases, maltogenic amylases and/or alpha-glucosidases; proteases; or mixtures of two of more thereof.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Methods and Materials
Measurement of Cellulase Activity Using Carboxy Methyl Cellulose (CMC) as Substrate The cellulytic activity may be measured in endo-glucanase units (EGU), determined at pH 6.0 with carboxy methyl cellulose (CMC) as substrate.

A substrate solution is prepared, containing 34.0 g/l CMC (Hercules 7 LFD) in 0.1 M phosphate buffer at pH 6.0. The enzyme sample to be analyzed is dissolved in the same buffer. 5 ml substrate solution and 0.15 ml enzyme solution are mixed and transferred to a vibration viscosimeter (e.g. MIVI 3000 from Sofraser, France), thermostated at 40° C. for 30 minutes.

One EGU is defined as the amount of enzyme that reduces the viscosity to one half under these conditions. The amount of enzyme sample should be adjusted to provide 0.01-0.02 EGU/ml in the reaction mixture. The arch standard is defined as 880 EGU/g.

Measurement of Cellulase Activity Using Filter Paper Assay (FPU Assay)

1. Source of Method
1.1 The method is disclosed in a document entitled "Measurement of Cellulase Activities" by Adney and Baker, 1996, Laboratory Analytical Procedure, LAP-006, National Renewable Energy Laboratory (NREL). It is based on the IUPAC method for measuring cellulase activity (Ghose, 1987, Measurement of Cellulase Activities, *Pure & Appl. Chem.* 59: 257-268.

2. Procedure
2.1 The method is carried out as described by Adney and Baker, 1996, supra, except for the use of a 96 well plates to read the absorbance values after color development, as described below.

2.2 Enzyme Assay Tubes:
2.2.1 A rolled filter paper strip (#1 Whatman; 1×6 cm; 50 mg) is added to the bottom of a test tube (13×100 mm).
2.2.2 To the tube is added 1.0 mL of 0.05 M Na-citrate buffer (pH 4.80).
2.2.3 The tubes containing filter paper and buffer are incubated 5 min. at 50° C. (±0.1° C.) in a circulating water bath.
2.2.4 Following incubation, 0.5 mL of enzyme dilution in citrate buffer is added to the tube. Enzyme dilutions are designed to produce values slightly above and below the target value of 2.0 mg glucose.
2.2.5 The tube contents are mixed by gently vortexing for 3 seconds.
2.2.6 After vortexing, the tubes are incubated for 60 mins. at 50° C. (±0.1° C.) in a circulating water bath.
2.2.7 Immediately following the 60 min. incubation, the tubes are removed from the water bath, and 3.0 mL of DNS reagent is added to each tube to stop the reaction. The tubes are vortexed 3 seconds to mix.

2.3 Blank and Controls
2.3.1 A reagent blank is prepared by adding 1.5 mL of citrate buffer to a test tube.
2.3.2 A substrate control is prepared by placing a rolled filter paper strip into the bottom of a test tube, and adding 1.5 mL of citrate buffer.
2.3.3 Enzyme controls are prepared for each enzyme dilution by mixing 1.0 mL of citrate buffer with 0.5 mL of the appropriate enzyme dilution.
2.3.4 The reagent blank, substrate control, and enzyme controls are assayed in the same manner as the enzyme assay tubes, and done along with them.

2.4 Glucose Standards
2.4.1 A 100 mL stock solution of glucose (10.0 mg/mL) is prepared, and 5 mL aliquots are frozen. Prior to use, aliquots are thawed and vortexed to mix.
2.4.2 Dilutions of the stock solution are made in citrate buffer as follows:

$G1$=1.0 mL stock+0.5 mL buffer=6.7 mg/mL=3.3 mg/0.5 mL $G2$=0.75 mL stock+0.75 mL buffer=5.0 mg/mL=2.5 mg/0.5 mL $G3$=0.5 mL stock+1.0 mL buffer=3.3 mg/mL=1.7 mg/0.5 mL $G4$=0.2 mL stock+0.8 mL buffer=2.0 mg/mL=1.0 mg/0.5 mL 2.4.3 Glucose standard tubes are prepared by adding 0.5 mL of each dilution to 1.0 mL of citrate buffer.
2.4.4 The glucose standard tubes are assayed in the same manner as the enzyme assay tubes, and done along with them.

2.5 Color Development
2.5.1 Following the 60 min. incubation and addition of DNS, the tubes are all boiled together for 5 mins. in a water bath.
2.5.2 After boiling, they are immediately cooled in an ice/water bath.
2.5.3 When cool, the tubes are briefly vortexed, and the pulp is allowed to settle. Then each tube is diluted by adding 50 microL from the tube to 200 microL of ddH$_2$O in a 96-well plate. Each well is mixed, and the absorbance is read at 540 nm.

2.6 Calculations (examples are given in the NREL document)
2.6.1 A glucose standard curve is prepared by graphing glucose concentration (mg/0.5 mL) for the four standards (G1-G4) vs. $A_{540}$. This is fitted using a linear regression (Prism Software), and the equation for the line is used to determine the glucose produced for each of the enzyme assay tubes.
2.6.2 A plot of glucose produced (mg/0.5 mL) vs. total enzyme dilution is prepared, with the Y-axis (enzyme dilution) being on a log scale.
2.6.3 A line is drawn between the enzyme dilution that produced just above 2.0 mg glucose and the dilution that produced just below that. From this line, it is determined the enzyme dilution that would have produced exactly 2.0 mg of glucose.
2.6.4 The Filter Paper Units/mL (FPU/mL) are calculated as follows:

FPU/mL=0.37/enzyme dilution producing 2.0 mg glucose

Enzymes Used

Cellulase preparation A: Cellulolytic composition comprising a polypeptide having cellulolytic enhancing activity (GH61A) disclosed in WO 2005/074656; an *Aspergillus oryzae* beta-glucosidase (in the fusion protein disclosed in U.S. 60/832,511), and a cellulolytic enzymes preparation derived from *Trichoderma reesei*. Cellulase preparation A is disclosed in co-pending U.S. application No. 60/941,251 which is hereby incorporated in entirety.

EXAMPLES

Example 1

Corn stover was pretreated using steam explosion at 200° C. for 5.4 min. The unwashed PCS (pretreated corn stover) was subjected to a fed-batch hydrolysis process starting with a batch hydrolysis comprising 50 g of water and substrate with an initial dry solids concentration of 12.60%. Cellulase composition A was used in a concentration of 200 EGU/g cellulose. The PCS was added in 3 additional loadings to a final dry solids concentration of 30%. The hydrolysis was performed at 50° C. and pH 5.0 for 120 hours.

The hydrolyzate was centrifuged at 5000 rpm for 20 min and the supernatant collected. Three concentration of hydrolyzates, namely 5% dry solids, 15% dry solids and 30% dry solids were produced by dilution with water and adjusted to pH 6.0 with 3M NaOH. Vials with 5 ml hydrolyzate each were inoculated with 1 g/L dry yeast (*Saccharomyces cerevisiae*) and fermented at 32° C. for 6 days. Samples of 10 ul were drawn daily for infection testing on nonselective Luria-Bertani (LB) plates. The plates were incubated at 37° C. overnight and the level of contamination was determined by colony count. Ethanol content was determined by HPLC. The results are presented in table 1 and 2.

TABLE 1

The contamination by bacteria at different dry solid levels during fermentation at pH 6

| Dry solids | 0 | 1 | 2 | 3 | 4 | 5 | 6 |
|---|---|---|---|---|---|---|---|
| 5% | 0 | 18 | 2680 | 179000 | 139100 | 78000 | 82200 |
| 15% | 0 | 500 | 36300 | 62000 | 118000 | 168000 | 60000 |
| 30% | 0 | 30 | 73 | 167 | 200 | 100 | 0 |

TABLE 2

The ethanol content at different dry solid levels during fermentation at pH 6

| Dry solids | 0 | 1 | 2 | 3 | 4 | 5 | 6 |
|---|---|---|---|---|---|---|---|
| 5% | 0 | 4.08 | 4.61 | 4.58 | 4.61 | 4.53 | 4.75 |
| 15% | 0 | 8.32 | 12.48 | 13.05 | 13.21 | 13.28 | 13.95 |
| 30% | 0 | 4.47 | 2.36 | 7.80 | 15.02 | 18.75 | 20.72 |

The results show that the high dry solids hydrolyzates can reduce the risk of contamination significantly when pH of fermentation is adjusted above 6.

Example 2

Corn stover was pretreated using steam explosion at 200° C. for 5.4 min. The unwashed PCS (pretreated corn stover) was subjected to a fed-batch hydrolysis process starting with a batch hydrolysis comprising 50 g of water and an initial dry solids concentration of 12.6%. Cellulase composition A was used in a concentration of 200 EGU/g cellulose. The PCS was added in 3 additional loadings to a final dry solids concentration of 30%. The hydrolysis was performed at 50° C. and pH 5.0 for 120 hours.

The hydrolyzate was centrifuged at 5000 rpm for 20 min and the supernatant collected. Two sets of four concentration of hydrolyzates, namely 5%, 15%, 25% and 30% dry solids were produced by dilution with water. One set was maintained at the natural pH 4.5 while another set was adjusted to pH 6.0 using 3M NaOH. Vials with 5 ml hydrolyzate each were inoculated with 5/L dry yeast (*Saccharomyces cerevisiae*) and fermented at 32° C. for 9 days. Samples of 10 microL were drawn daily for plating on nonselective Luria-Bertani (LB) plates. The plates were incubated at 37° C. overnight and the level of contamination was determined by colony count. Ethanol content was determined by HPLC. The results are presented in tables 3 to 6

TABLE 3

Contamination by bacteria at different dry solid (DS) levels during fermentation at pH 4.5.

| Dry solids | 0 | 1 | 2 | 3 | 4 | 5 | 6 | 7 | 8 | 9 |
|---|---|---|---|---|---|---|---|---|---|---|
| 5% | 0 | 0 | 6 | 6 | 6 | 6 | 6 | 6 | 6 | 6 |
| 15% | 0 | 0 | 0 | 0 | 0 | 0 | 0 | 0 | 0 | 0 |
| 25% | 0 | 0 | 0 | 0 | 0 | 0 | 0 | 0 | 0 | 0 |
| 30% | 0 | 0 | 0 | 0 | 0 | 0 | 0 | 0 | 0 | 0 |

$0 = 0$, $1 = 1 \geq 10$, $2 = 10 \geq 100$, $3 = 100 \geq 1000$, $4 = 1000 \geq 10000$, $5 = 10000 \geq 100000$, $6 = 100000 \geq 1000000$ cell/ml.

TABLE 4

Contamination by bacteria at different dry solid (DS) levels during fermentation at pH 6.

| Dry solids | 0 | 1 | 2 | 3 | 4 | 5 | 6 | 7 | 8 | 9 |
|---|---|---|---|---|---|---|---|---|---|---|
| 5% | 0 | 3 | 4 | 4 | 6 | 6 | 6 | 6 | 6 | 6 |
| 15% | 0 | 4 | 4 | 5 | 6 | 6 | 6 | 6 | 6 | 5 |
| 25% | 0 | 1 | 0 | 3 | 3 | 4 | 3 | 3 | 0 | 2 |
| 30% | 0 | 1 | 0 | 3 | 3 | 5 | 4 | 3 | 3 | 2 |

$0 = 0$, $1 = 1 \geq 10$, $2 = 10 \geq 100$, $3 = 100 \geq 1000$, $4 = 1000 \geq 10000$, $5 = 10000 \geq 100000$, $6 = 100000 \geq 1000000$ cell/ml.

TABLE 5

Ethanol content (g/L) of three samples with different dry solid (DS) at pH 4.5

| Dry solids | 0 | 1 | 2 | 3 | 4 | 5 | 6 | 7 | 8 | 9 |
|---|---|---|---|---|---|---|---|---|---|---|
| 5% | 0 | 6.6 | 9.6 | 9.7 | 8.6 | 8.3 | 8.5 | 8.3 | 7.8 | 7.7 |
| 15% | 0 | 2.7 | 10.4 | 23.8 | 24.8 | 25.8 | 27.1 | 26.9 | 25.5 | 26.7 |
| 25% | 0 | 1.0 | 1.0 | 1.3 | 0.7 | 1.1 | 1.4 | 0.8 | 0.8 | 0.8 |
| 30% | 0 | 2.1 | 1.7 | 1.1 | 1.0 | 1.1 | 1.6 | 1.0 | 1.3 | 1.1 |

TABLE 6

Ethanol content (g/L) of three samples with different dry solid (DS) at pH 6

| Dry solids | 0 | 1 | 2 | 3 | 4 | 5 | 6 | 7 | 8 | 9 |
|---|---|---|---|---|---|---|---|---|---|---|
| 5% | 0 | 8.1 | 8.3 | 8.2 | 8.2 | 8.2 | 7.4 | 7.4 | 7.0 | 6.2 |
| 15% | 0 | 21.8 | 24.6 | 24.5 | 24.7 | 23.9 | 22.2 | 21.2 | 20.1 | 18.3 |
| 25% | 0 | 12.4 | 35.2 | 37.2 | 37.1 | 40.0 | 40.8 | 40.6 | 41.3 | 40.9 |
| 30% | 0 | 3.0 | 9.8 | 20.6 | 30.8 | 37.2 | 40.5 | 42.3 | 44.9 | 44.2 |

The level of contamination at the low dry solids concentrations (5% dry solids and 15% dry solids) increase when pH is raised from 4.5 to 6. However, the contamination at pH 6 can be significantly inhibited by increasing the concentration of dry solids, such as to 25% or 30% dry solids. Furthermore, by raising the pH from 4.5 to 6.0 the fermentation at 25% dry solids and at 30% dry solids is improved dramatically. Apparently, the increased inhibitor concentration in high dry solids hydrolyzates reduces the level of bacterial contamination. This allows applying a higher pH during fermentation which improves yeast growth.

Example 3

Corn stover was pretreated using steam explosion at 200° C. for 5.4 min. The unwashed PCS was subjected to a fed-batch hydrolysis process starting with a batch hydrolysis comprising 50 g of water and substrate with initial dry solids concentration of 12.6%. Cellulase composition A was utilized for enzymatic hydrolysis in a concentration of 200 EGU/g cellulose. Unwashed PCS was added in 3 additional loadings to a final dry solids concentration of 30%. The hydrolysis was performed at 50° C. and pH 5.0 for 120 hours.

The hydrolyzate was centrifuged at 5000 rpm for 20 min and the supernatant collected. Three concentration of hydrolyzates, namely 5% dry solids, 10% dry solids, 15% dry solids, 20% dry solids, 25% dry solids and 30% dry solids were produced by dilution with water and adjusted to pH 4.5, 5.0, 6.0, 7.0, 8.0 and 9.0 with 3M NaOH. Vials with 5 ml hydrolyzate each were inoculated with 1 g/L dry yeast (Saccharomyces cerevisiae) and fermented at 32° C. for 10 days. Samples of 10 microL were drawn daily for plating on non-selective Luria-Bertani (LB) plates. The plates were incubated at 37° C. overnight and the level of contamination was determined by colony count. Ethanol content was determined by weight of carbon dioxide loss (EtOH (g/L)=(weight loss× 1.05×1000)/(system weight)). The results are presented in table 7-18.

The results show the risk of contamination during fermentation at pH of around 6 and above, e.g. from 5.5 to 9.0, can be significantly reduce if the dry solids of hydrolyzates is around 20% and above, such as from 17.5 to 30%.

TABLE 7

The ethanol content (g/L) of 5% dry solids hydrolysates by bacteria at different pH.

| pH | Fermentation time (days) | | | | | | | | | | |
|---|---|---|---|---|---|---|---|---|---|---|---|
| | 0 | 1 | 2 | 3 | 4 | 5 | 6 | 7 | 8 | 9 | 10 |
| 4.5 | 0 | 9.4 | 9.4 | 9.3 | 10.5 | 11.9 | 13.1 | 14.2 | 15.4 | 16.2 | 17.3 |
| 5.0 | 0 | 9.1 | 9.7 | 9.4 | 10.7 | 12.0 | 13.1 | 14.2 | 15.3 | 16.0 | 17.1 |
| 6.0 | 0 | 8.6 | 8.5 | 7.6 | 8.7 | 9.9 | 11.0 | 11.9 | 12.9 | 13.4 | 14.3 |
| 7.0 | 0 | 8.2 | 8.2 | 7.5 | 8.6 | 9.8 | 10.8 | 11.6 | 12.6 | 12.3 | 13.2 |
| 8.0 | 0 | 8.1 | 8.1 | 7.2 | 8.3 | 9.5 | 10.4 | 11.2 | 12.5 | 12.3 | 13.4 |
| 9.0 | 0 | 8.0 | 8.1 | 7.2 | 8.5 | 9.9 | 11.2 | 12.2 | 13.4 | 14.0 | 15.1 |

TABLE 8

The contamination of 5% dry solids hydrolysates by bacteria at different pH.

| pH | Fermentation time (days) | | | | | | | | | | |
|---|---|---|---|---|---|---|---|---|---|---|---|
| | 0 | 1 | 2 | 3 | 4 | 5 | 6 | 7 | 8 | 9 | 10 |
| 4.5 | 0 | 0 | 2 | 5 | 5 | 6 | 6 | 6 | 6 | 6 | 6 |
| 5.0 | 0 | 0 | 2 | 5 | 6 | 6 | 6 | 6 | 6 | 6 | 6 |
| 6.0 | 0 | 1 | 5 | 6 | 6 | 6 | 6 | 6 | 6 | 6 | 6 |
| 7.0 | 0 | 4 | 6 | 6 | 6 | 6 | 6 | 6 | 6 | 6 | 6 |
| 8.0 | 0 | 4 | 5 | 6 | 6 | 6 | 6 | 6 | 6 | 6 | 6 |
| 9.0 | 0 | 5 | 6 | 6 | 6 | 6 | 6 | 6 | 6 | 6 | 6 |

0 = 0, 1 = 1 > 10, 2 = 10 > 100, 3 = 100 > 1000, 4 = 1000 > 10000, 5 = 10000 > 100000, 6 = 100000 > 1000000 cell/ml.

TABLE 9

The ethanol content (g/L) of 10% dry solids hydrolysates at different pH.

| pH | Fermentation time (days) | | | | | | | | | | |
|---|---|---|---|---|---|---|---|---|---|---|---|
| | 0 | 1 | 2 | 3 | 4 | 5 | 6 | 7 | 8 | 9 | 10 |
| 4.5 | 0 | 4.3 | 15.9 | 16.5 | 18.9 | 21.2 | 23.2 | 25.1 | 27.0 | 28.2 | 30.2 |
| 5.0 | 0 | 16.2 | 18.4 | 18.6 | 20.9 | 23.1 | 25.1 | 26.9 | 28.8 | 29.8 | 31.6 |
| 6.0 | 0 | 15.2 | 17.5 | 17.6 | 19.7 | 21.5 | 23.3 | 24.8 | 26.5 | 27.3 | 29.1 |
| 7.0 | 0 | 15.1 | 17.8 | 18.4 | 20.5 | 22.6 | 24.5 | 26.0 | 27.7 | 28.4 | 30.1 |
| 8.0 | 0 | 14.3 | 17.1 | 17.8 | 19.8 | 21.6 | 23.6 | 25.2 | 27.1 | 27.9 | 29.8 |
| 9.0 | 0 | 12.5 | 15.7 | 16.3 | 18.4 | 20.3 | 22.4 | 23.9 | 25.5 | 26.1 | 27.8 |

TABLE 10

The contamination of 10% dry solids hydrolysates by bacteria at different pH.

| pH | Fermentation time (days) | | | | | | | | | | |
|---|---|---|---|---|---|---|---|---|---|---|---|
|  | 0 | 1 | 2 | 3 | 4 | 5 | 6 | 7 | 8 | 9 | 10 |
| 4.5 | 0 | 0 | 2 | 5 | 0 | 0 | 0 | 2 | 1 | 0 | 0 |
| 5.0 | 0 | 0 | 1 | 0 | 4 | 5 | 6 | 6 | 6 | 6 | 6 |
| 6.0 | 0 | 2 | 1 | 6 | 6 | 6 | 6 | 6 | 6 | 6 | 6 |
| 7.0 | 0 | 4 | 2 | 6 | 6 | 6 | 6 | 6 | 6 | 6 | 6 |
| 8.0 | 0 | 2 | 2 | 2 | 2 | 5 | 6 | 6 | 6 | 6 | 6 |
| 9.0 | 0 | 5 | 6 | 6 | 6 | 6 | 6 | 6 | 6 | 6 | 6 |

0 = 0, 1 = 1 > 10, 2 = 10 > 100, 3 = 100 > 1000, 4 = 1000 > 10000, 5 = 10000 > 100000, 6 = 100000 > 1000000 cell/ml.

TABLE 11

The ethanol content (g/L) of 15% dry solids hydrolysates at different pH.

| pH | Fermentation time (day) | | | | | | | | | | |
|---|---|---|---|---|---|---|---|---|---|---|---|
|  | 0 | 1 | 2 | 3 | 4 | 5 | 6 | 7 | 8 | 9 | 10 |
| 4.5 | 0 | 0.4 | 0 | 0 | 7.1 | 9.1 | 14.8 | 20.2 | 22.7 | 24.1 | 27.6 |
| 5.0 | 0 | 9.9 | 26.0 | 28.4 | 31.8 | 34.9 | 38.2 | 41.0 | 44.2 | 46.1 | 49.4 |
| 6.0 | 0 | 19.5 | 26.8 | 29.1 | 32.4 | 35.4 | 38.5 | 41.2 | 43.9 | 45.6 | 48.2 |
| 7.0 | 0 | 18.1 | 26.2 | 28.7 | 32.2 | 34.8 | 37.6 | 40.1 | 42.4 | 43.6 | 46.1 |
| 8.0 | 0 | 16.2 | 24.4 | 26.7 | 29.9 | 32.6 | 35.3 | 37.6 | 39.9 | 40.9 | 43.3 |
| 9.0 | 0 | 14.2 | 22.9 | 25.5 | 28.7 | 31.5 | 34.2 | 36.6 | 39.3 | 40.6 | 43.5 |

TABLE 12

The contamination of 15% dry solids hydrolysates by bacteria at different pH.

| pH | Fermentation time (day) | | | | | | | | | | |
|---|---|---|---|---|---|---|---|---|---|---|---|
|  | 0 | 1 | 2 | 3 | 4 | 5 | 6 | 7 | 8 | 9 | 10 |
| 4.5 | 0 | 2 | 2 | 2 | 0 | 0 | 0 | 0 | 0 | 0 | 1 |
| 5.0 | 0 | 0 | 0 | 1 | 0 | 0 | 2 | 0 | 0 | 0 | 4 |
| 6.0 | 0 | 0 | 3 | 3 | 6 | 6 | 6 | 5 | 6 | 2 | 6 |
| 7.0 | 0 | 0 | 3 | 2 | 6 | 6 | 6 | 5 | 6 | 5 | 6 |
| 8.0 | 0 | 3 | 2 | 6 | 6 | 6 | 6 | 6 | 6 | 5 | 6 |
| 9.0 | 0 | 0 | 5 | 6 | 6 | 6 | 6 | 6 | 6 | 5 | 6 |

0 = 0, 1 = 1 > 10, 2 = 10 > 100, 3 = 100 > 1000, 4 = 1000 > 10000, 5 = 10000 > 100000, 6 = 100000 > 1000000 cell/ml.

TABLE 13

The ethanol content (g/L) of 20% dry solids hydrolysates at different pH.

| pH | Fermentation time (day) | | | | | | | | | | |
|---|---|---|---|---|---|---|---|---|---|---|---|
|  | 0 | 1 | 2 | 3 | 4 | 5 | 6 | 7 | 8 | 9 | 10 |
| 4.5 | 0 | 0.229 | 0 | 0 | 0 | 0 | 0 | 0 | 0 | 0 | 0 |
| 5.0 | 0 | 0.599 | 0 | 12.61 | 28.43 | 41.24 | 46.68 | 50.66 | 54.75 | 57.22 | 61.57 |
| 6.0 | 0 | 13.68 | 31.78 | 35.74 | 40.05 | 43.92 | 47.66 | 51.25 | 55.21 | 57.66 | 61.5 |
| 7.0 | 0 | 11.5 | 29.95 | 34.43 | 38.74 | 42.62 | 46.37 | 49.92 | 47.05 | 49.48 | 53.4 |
| 8.0 | 0 | 11.28 | 28.93 | 34.03 | 39.16 | 43.37 | 46.93 | 50.08 | 53.42 | 55.52 | 59.04 |
| 9.0 | 0 | 10.77 | 26 | 30.88 | 34.92 | 38.32 | 41.7 | 44.77 | 48.22 | 50.39 | 54.68 |

TABLE 14

The contamination of 20% dry solids hydrolysates by bacteria at different pH.

| pH | \multicolumn{11}{c|}{Fermentation time (day)} |
|---|---|---|---|---|---|---|---|---|---|---|---|
|    | 0 | 1 | 2 | 3 | 4 | 5 | 6 | 7 | 8 | 9 | 10 |
| 4.5 | 0 | 2 | 0 | 2 | 0 | 3 | 0 | 1 | 0 | 0 | 0 |
| 5.0 | 0 | 0 | 0 | 2 | 2 | 0 | 0 | 0 | 5 | 0 | 4 |
| 6.0 | 0 | 0 | 0 | 0 | 0 | 0 | 3 | 0 | 2 | 5 | 1 |
| 7.0 | 0 | 2 | 1 | 2 | 2 | 2 | 6 | 6 | 3 | 5 | 5 |
| 8.0 | 0 | 2 | 3 | 4 | 5 | 2 | 6 | 5 | 6 | 6 | 5 |
| 9.0 | 0 | 3 | 3 | 4 | 2 | 6 | 6 | 5 | 6 | 6 | 5 |

0 = 0, 1 = 1 > 10, 2 = 10 > 100, 3 = 100 > 1000, 4 = 1000 > 10000, 5 = 10000 > 100000, 6 = 100000 > 1000000 cell/ml.

TABLE 15

The ethanol content (g/L) of 25% dry solids hydrolysates at different pH.

| pH | \multicolumn{11}{c|}{Fermentation time (day)} |
|---|---|---|---|---|---|---|---|---|---|---|---|
|    | 0 | 1 | 2 | 3 | 4 | 5 | 6 | 7 | 8 | 9 | 10 |
| 4.5 | 0 | 0.2 | 0 | 0 | 0 | 0 | 0 | 0 | 0 | 0 | 0 |
| 5.0 | 0 | 0.2 | 0 | 0 | 0 | 0 | 0 | 0 | 0 | 0 | 0 |
| 6.0 | 0 | 0.6 | 0 | 0 | 4.2 | 10.9 | 19.1 | 26.6 | 33.8 | 38.3 | 44.0 |
| 7.0 | 0 | 0.5 | 0 | 2.7 | 13.6 | 26.7 | 37.2 | 45.3 | 52.2 | 56.3 | 61.8 |
| 8.0 | 0 | 1.5 | 10.6 | 23.7 | 34.5 | 41.6 | 47.2 | 51.8 | 56.2 | 58.8 | 62.9 |
| 9.0 | 0 | 0.7 | 9.1 | 22.7 | 33.5 | 40.3 | 46.3 | 50.9 | 55.1 | 57.6 | 61.8 |

TABLE 16

The contamination of 25% dry solids hydrolysates by bacteria at different pH.

| pH | \multicolumn{11}{c|}{Fermentation time (day)} |
|---|---|---|---|---|---|---|---|---|---|---|---|
|    | 0 | 1 | 2 | 3 | 4 | 5 | 6 | 7 | 8 | 9 | 10 |
| 4.5 | 0 | 0 | 3 | 0 | 0 | 0 | 0 | 0 | 0 | 0 | 0 |
| 5.0 | 0 | 0 | 3 | 0 | 0 | 0 | 0 | 0 | 0 | 0 | 0 |
| 6.0 | 0 | 2 | 2 | 0 | 0 | 0 | 3 | 1 | 0 | 0 | 0 |
| 7.0 | 0 | 2 | 0 | 0 | 0 | 0 | 0 | 3 | 2 | 0 | 0 |
| 8.0 | 0 | 1 | 0 | 0 | 0 | 0 | 0 | 3 | 0 | 0 | 0 |
| 9.0 | 0 | 2 | 1 | 0 | 0 | 0 | 0 | 1 | 0 | 0 | 0 |

0 = 0, 1 = 1 > 10, 2 = 10 > 100, 3 = 100 > 1000, 4 = 1000 > 10000, 5 = 10000 > 100000, 6 = 100000 > 1000000 cell/ml.

TABLE 17

The ethanol content (g/L) of 30% dry solids hydrolysates at different pH.

| pH | \multicolumn{11}{c|}{Fermentation time (day)} |
|---|---|---|---|---|---|---|---|---|---|---|---|
|    | 0 | 1 | 2 | 3 | 4 | 5 | 6 | 7 | 8 | 9 | 10 |
| 4.5 | 0 | 0.1 | 0 | 0 | 0 | 0 | 0 | 0 | 0.9 | 0 | 0.3 |
| 5.0 | 0 | 0.2 | 0 | 0 | 0 | 0 | 0 | 0 | 0 | 0 | 0 |
| 6.0 | 0 | 0.6 | 0 | 0.8 | 6.8 | 14.4 | 22.5 | 29.7 | 36.9 | 41.4 | 47.4 |
| 7.0 | 0 | 0.4 | 0 | 1.8 | 11.3 | 23.4 | 35.0 | 44.2 | 51.7 | 56.1 | 61.7 |
| 8.0 | 0 | 1.1 | 7.9 | 20.3 | 31.4 | 39.1 | 45.5 | 50.9 | 55.8 | 59.1 | 64.1 |
| 9.0 | 0 | 0.8 | 9.1 | 20.9 | 30.7 | 38.1 | 44.0 | 48.9 | 53.6 | 56.4 | 61.1 |

TABLE 18

The contamination of 30% dry solids hydrolysates by bacteria at different pH.

| pH | \multicolumn{11}{c|}{Fermentation time (day)} |
|---|---|---|---|---|---|---|---|---|---|---|---|
|    | 0 | 1 | 2 | 3 | 4 | 5 | 6 | 7 | 8 | 9 | 10 |
| 4.5 | 0 | 0 | 3 | 0 | 0 | 0 | 4 | 3 | 0 | 0 | 0 |
| 5.0 | 0 | 0 | 3 | 0 | 0 | 0 | 3 | 0 | 0 | 0 | 0 |
| 6.0 | 0 | 3 | 0 | 0 | 0 | 3 | 0 | 0 | 0 | 0 | 0 |
| 7.0 | 0 | 0 | 0 | 0 | 0 | 0 | 0 | 0 | 0 | 0 | 0 |
| 8.0 | 0 | 4 | 0 | 0 | 0 | 0 | 0 | 4 | 0 | 0 | 0 |
| 9.0 | 0 | 0 | 0 | 0 | 0 | 3 | 0 | 4 | 0 | 0 | 0 |

0 = 0, 1 = 1 > 10, 2 = 10 > 100, 3 = 100 > 1000, 4 = 1000 > 10000, 5 = 10000 > 100000, 6 = 100000 > 1000000 cell/ml.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

The invention claimed is:
1. A process for producing a fermentation product, comprising:
    (a) pre-treating a lignocellulose-containing material;
    (b) hydrolyzing the pre-treated lignocellulose-containing material; and
    (c) fermenting the hydrolyzate obtained in step (a) using a yeast; wherein during fermentation, the pH is from 6.0 to 9.0 and the dry solids concentration is at least 20%.
2. The process of claim 1, wherein the pH during fermentation is in the range of 6.0 to 8.0.
3. The process of claim 1, wherein the pH during fermentation is in the range of 6.0 to 7.0.
4. The process of claim 1, wherein the pH during fermentation is in the range of 6.0 to 6.5.
5. The process of claim 1, wherein the pH during fermentation is around pH 6.
6. The process of claim 1, wherein the dry solids concentration during fermentation is in the range of 20 to 35%.
7. The process of claim 1, wherein the dry solids concentration during fermentation is in the range of 25 to 35%.
8. The process of claim 1, wherein the dry solids concentration during fermentation is in the range of 30 to 35%.
9. The process of claim 1, wherein the dry solids concentration during fermentation is in the range of 33 to 35%.
10. The process of claim 1, wherein the lignocellulose-containing material is derived from corn, such as corn stover, and/or corn fiber.
11. The process of claim 1, wherein the enzymatic hydrolysis and/or fermentation is carried out using one or more hydrolases selected from the group consisting of endoglucanase, beta-glucosidase, cellobiohydrolase, cellobiase, xylanase, alpha-amylase, alpha-glucosidase, glucoamylase, proteases and lipases, or a mixture thereof.
12. The process of claim 1, wherein the fermentation product is an alcohol.
13. The process of claim 1, wherein the fermentation product is ethanol.
14. The process of claim 1, further comprising recovering the fermentation product.
15. A process for producing a fermentation product, comprising,
    contacting a hydrolyzate of a pre-treated lignocellulose-containing material with a yeast to produce a fermentation product,
    wherein during fermentation, the pH is from 6.0 to 9.0 and the dry solids concentration is at least 20%.
16. The process of claim 15, wherein the hydrolyzate is produced by acid hydrolysis of a lignocellulose-containing material.
17. The process of claim 15, wherein the hydrolyzate is produced by enzymatic hydrolysis of a lignocellulose-containing material.

* * * * *